US008420362B2

United States Patent
Crawford et al.

(10) Patent No.: US 8,420,362 B2
(45) Date of Patent: Apr. 16, 2013

(54) IN SITU PRECIPITATION OF CALCIUM CARBONATE (CACO₃) BY INDIGENOUS MICROORGANISMS TO IMPROVE MECHANICAL PROPERTIES OF A GEOMATERIAL

(75) Inventors: Ronald L. Crawford, Moscow, ID (US); Malcolm B. Burbank, Pullman, WA (US); Thomas J. Weaver, Moscow, ID (US); Barbara C. Williams, Viola, ID (US)

(73) Assignee: University of Idaho, Moscow, ID (US)

( * ) Notice: Subject to any disclaimer, the term of this patent is extended or adjusted under 35 U.S.C. 154(b) by 266 days.

(21) Appl. No.: 12/802,103

(22) Filed: May 28, 2010

(65) Prior Publication Data

US 2011/0027850 A1 Feb. 3, 2011

Related U.S. Application Data

(60) Provisional application No. 61/230,952, filed on Aug. 3, 2009.

(51) Int. Cl.
*C12P 3/00* (2006.01)
*C12N 9/00* (2006.01)
*C12N 1/20* (2006.01)
*C12N 15/00* (2006.01)

(52) U.S. Cl.
USPC ...... 435/168; 435/183; 435/252.3; 435/320.1

(58) Field of Classification Search .......... None
See application file for complete search history.

(56) References Cited

U.S. PATENT DOCUMENTS

2008/0245272 A1 10/2008 Kucharski

FOREIGN PATENT DOCUMENTS

WO   WO 2008/120979   10/2008

OTHER PUBLICATIONS

Ciurli et al. Soil Biology and Biochemistry. vol. 28, Issue 6, Jun. 1996, pp. 811-817.*
Rodriguez-Navaro, C., "Conservation of Ornamental Stone by *Myxociccus xanthus*-Induced Carbonate Biomineralization." Appl. Environ. Microbiol., 69(4):2182-2193 (2003).
Fujita, Y, et al, "Calcium carbonat precipitation by ureolytic subsurface bacteria," Geomicobiology Journal, 17:305-318 (2000).
Fujita, Y, et al, "Stimulation fo microbial urea hydrolysis in groundwater to enhance calcite precipitation," Environ. Sci. Technol., 42:3025-3032 (2008).
DeJong, JT, et al, "Microbially induced cementation to control sand response to undrained shear," J. Geotechnical and Geoenvironmental Engineering, 132(11):1381-1392 (2006).
Whiffen, VS, et al, "Microbial carbonate precipitation as a soil improvement technique," Geomicrobiology Journal, 24:417-423 (2007).
Stocks-Fischer, S, et al, "Microbiological precipitation of CaCO3," Soil Biology and Biochemistry, 31:1563-1571 (1999).
Van Paassen, LA, et al, "Scale up of BioGrout: a biological ground reinforcement method," Proceedings of the 17th Intl Conf. on Soil Mechs. and Geotechnical Eng. (2009).
Colwell, FS, et al, "Microbially mediated . . . ", Chapter 6, pp. 117-137 in Subsurface Contamination Remediation, ACS Symposium Series, American Chemical Society, (2005).
Whiffen, VS, "Microbial CaCO3 precipitation for the production of biocement," Doctoral Thesis, Murdoch University, Perth, Western Australia (2004).

\* cited by examiner

*Primary Examiner* — Christian Fronda
(74) *Attorney, Agent, or Firm* — Howard Eisenberg, Esq.

(57) ABSTRACT

A method for increasing the concentration of calcium carbonate in a geomaterial that contains indigenous microorganisms capable of hydrolyzing urea to ammonia, which method includes enriching the geomaterial with a source of nutrients, adding urea to the geomaterial which is hydrolyzed to ammonia and which raises the pH of the geomaterial, and adding a source of calcium ions to the geomaterial. Carbonate ions obtained by the hydrolysis of the urea combine with calcium ions to form calcium carbonate.

11 Claims, No Drawings

IN SITU PRECIPITATION OF CALCIUM CARBONATE (CACO₃) BY INDIGENOUS MICROORGANISMS TO IMPROVE MECHANICAL PROPERTIES OF A GEOMATERIAL

This application claims priority from U.S. Provisional Patent Application Ser. No. 61/230,952, filed Aug. 3, 2009, which provisional patent application is incorporated herein in its entirety.

STATEMENT OF FEDERAL SUPPORT

Pursuant to 35 U.S.C. §202, it is hereby acknowledged that the U.S. Government has certain rights in the invention described herein, which was supported by Grant No. 0700918 from the National Science Foundation.

FIELD OF THE INVENTION

The present invention pertains to the field of forming cement in porous geomaterials utilizing microorganisms that hydrolyze urea.

BACKGROUND OF THE INVENTION

Cementation is the process of deposition of dissolved mineral components in the interstices of porous materials followed by the sticking together of material to form a cemented material. In nature, cementation is a geological process by which sedimentary rocks such as sandstone and limestone are formed. Sandstone and limestone are formed primarily through the precipitation of calcite cement.

Calcite is the least soluble and most stable polymorph of calcium carbonate. Other polymorphs of calcium carbonate are aragonite and vaterite. Supersaturated solutions of calcium carbonate precipitate as unstable amorphous calcium carbonate which is spontaneously converted to the metastable polymorph vaterite. Conversion of vaterite to calcite occurs rapidly in the presence of water, with almost all vaterite converting to calcite within a period of 24 hours. In soil, calcite bridges adjacent soil particles, cementing soil grains together to form a cemented sand or sandstone. In addition to cementing soil grains together, fine particulate $CaCO_3$ can reduce the pore space in the soil matrix and increase the soil's ability to resist shear.

Many naturally occurring microorganisms present in soils, especially bacteria of the family Bacillacae such as bacteria of the genera *Bacillus, Sporosarcina, Sporolactobacillus, Clostridium* and *Desulfotomaculum* are able to hydrolyze urea $(NH_2)_2CO$ in the presence of water to ammonium and carbonate ions by the following reaction.

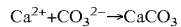

$(NH_2)_2CO + 2H_2O \rightarrow 2NH_4^+ + CO_3^{2-}$

The generation of $NH_4^+$ ions increases local pH and, in the presence of calcium ions and the availability of nucleation sites, the carbonate ions react spontaneously with the calcium ions to form calcium carbonate by the following reaction.

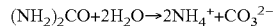

$Ca^{2+} + CO_3^{2-} \rightarrow CaCO_3$

Because calcium carbonate will spontaneously form the stable polymorph calcite which cements soil grains together, microbial cementation has been conceived to be useful in many applications. Kucharski, U.S. patent application Ser. No. 2008/0245272 discloses that microbial biocementation can be used for civil engineering applications such as for fabricating, stabilizing, and reinforcing retaining walls, embankments, and tunnels of for stabilizing sands in earthquake zones at risk of liquefaction, for mining applications such as to provide support for ground that is broken during mining, to strengthen tailing dams to prevent erosion, and to bind dust particles, for construction applications such as to create "instant" pavements such as roads and runways, for restoration applications such as to preserve, restore, and strengthen weathered mortar and masonry, for environmental applications such as the stabilization and removal of pollutants such as heavy metals, fibers, and radioactive elements, and the control of erosion, and for other uses such as the creation of filters including the immobilization of bacteria into a cemented biofilter.

Kucharski discloses a method for forming a cement by combining a starting material such as rock, sand, soil, or clay with particular amounts of (1) an exogenous microorganism that is capable of producing urease, (2) urea, and (3) calcium ions. The method of Kucharski, however, presents several disadvantages, some of which are dealt with in the Kucharski application itself.

One disadvantage is that, due to the fact that the three above components are injected into the starting material and that calcite formation rapidly occurs in such circumstances, calcite formation and resultant cementation tends to concentrate at or near the point of injection of the three components into the starting material. This problem is discussed in Whiffin et al, "Microbial Carbonate Precipitation as a Soil Improvement Technique," Geomicrobiology Journal, 24:417-423 (2007). Whiffin, also one of the co-inventors in the Kucharski application, discloses that injection of bacteria together with reagents can result in clogging of the system near the injection point due to the rapid production of calcite. Whiffin discloses a process by which bacteria and reagents may be injected into a starting material without clogging of the material. However, in FIG. 5 on page 420, Whiffin shows that, although an average column volume of 59.2 kg $CaCO_3/m^3$ was obtained, the distribution of calcium carbonate in the column was very uneven with values of more than twice the average occurring at a distance of 100 cm from the injection point. Thus, even though clogging did not occur, the method of Whiffin results in an uneven distribution of calcite throughout a starting material and thus in uneven strengthening throughout the starting material.

A second disadvantage of the method of Kucharski is that of loss of microorganisms following their addition to the starting material, discussed in Kucharski in paragraph 0072. Kucharski discloses that this problem may be dealt with by fixing the microorganisms in the starting material prior to cementation. Thus, as stated in paragraph 0072, the method of Kucharski involves the sequential steps of (1) applying the microorganism to the starting material, (2) fixing the microorganism in the starting material, and (3) then combining the starting material incorporating the fixed microorganisms with urea and calcium ions.

A third disadvantage of Kucharski is that, by necessity, the method of Kucharski utilizes a finite number of microbial species, and typically utilizes only one microbial species. Natural environments such as soil contain numerous microbial species that exist in a complex ecological framework. Injection of a monoculture or of a culture containing several microbial species disrupts the ecological framework that existed prior to injection. Moreover, microbes that are injected into a starting material are at a competitive disadvantage to organisms already present that are adapted to the local environment, resulting in loss of a large portion of the injection microbes.

Additionally, because different microbial organisms are able to produce calcite at different optimum values of pH, pH and other environmental parameters must be optimized depending on the particular microorganism that is injected into the starting material.

These disadvantages of Kucharski render the method disclosed therein unpractical for many applications. A significant need exists, therefore, for a method of microbial biocementation that overcomes the disadvantages of the prior art.

DESCRIPTION OF THE INVENTION

It has been unexpectedly discovered that the process of microbial biocementation can be made to be practical and useful in real world applications by utilizing indigenous urea-hydrolyzing microorganisms such as bacteria that are present in virtually all geomaterials such as soil and rock, or natural waters such as aquifers. Thus, in one embodiment, the invention is a method for increasing the concentration of calcium carbonate in a geomaterial. According to this embodiment of the present method, the concentration of calcium carbonate in a geomaterial is increased by enhancing the growth of ureolytic microorganisms within the geomaterial and providing to the ureolytic microorganisms within the geomaterial urea and a source of calcium ions wherein the urea is converted by the ureolytic microorganisms to ammonium and carbonate ions and the carbonate ions combine with the calcium ions to form calcium carbonate.

In a preferred embodiment, the growth of microorganisms within a geomaterial is promoted by adding to the geomaterial a source of nutrients that supports the growth of microorganisms that are capable of living under conditions of high urea concentration and high pH. This growth is encouraged by adding to the geomaterial a carbon source and urea that promote the growth of indigenous alkalinity-tolerant and ureolytic microorganisms. The production of calcium carbonate by microorganisms in the geomaterial is promoted by adding to the soil a source of calcium ions, which spontaneously forms calcite which serves to cement the geomaterial. According to this method, it is preferred that no exogenous urea-hydrolyzing microorganisms are added to the geomaterial. The lack of addition of exogenous microorganisms refers to such organisms that are deliberately added to a geomaterial. Because microorganisms are ubiquitous, it is understood that exogenous microorganisms, such as on those present on the hands of individuals working with a geomaterial, may inadvertently be added to the geomaterial. Such inadvertent addition of exogenous microorganisms is considered to be a contaminant that is difficult if not impossible to avoid and, therefore, when referring to exogenous microorganisms that are or are not added to a geomaterial, it is the deliberate addition of exogenous microorganisms that is contemplated.

The term "geomaterial" means a geologic or geologically derived material, examples of which include soil and rock.

The term "reactants" is used to refer individually or collectively to the materials that are added to the geomaterial in accordance with the present method.

The term "indigenous" when referring to microorganisms means originating and living or occurring naturally in an area or environment and excludes microorganisms that have been exogenously added to the area or environment unless such exogenously added microorganisms had been added to the area or environment at a time sufficiently distant in the past to permit the added microorganisms to adapt to the area or environment. For purposes of this application. a microorganism is considered to be indigenous if it was added to a geomaterial at least one week ago. Likewise, a microorganism is considered to be exogenous if it was added to a geomaterial less than one week ago.

Although it is preferred that no exogenous microorganisms are added to a geomaterial when performing the present invention, the utilization of exogenous microorganisms in addition to performing the steps of the present method is considered to be within the scope of the present method, so long as the steps of the present method are performed.

Although microorganisms in a geomaterial typically directly produce forms of calcium carbonate other than calcite, such other forms of calcium carbonate are spontaneously converted to calcite, either directly or indirectly, in the presence of water at ambient temperatures less than about 60° C. Therefore, the terms "calcium carbonate" and "calcite" when referring to products produced by microorganisms in the soil are used herein interchangeably unless stated otherwise or necessitated by context.

The presently disclosed method overcomes many of the disadvantages of the prior art. The present method avoids the problem of clogging at the injection site associated with prior art methods that occurs due to the rapid production of calcite when bacteria are injected with a source of calcium and urea. The present method also avoids the problem of uneven distribution of calcite production within a geomaterial which likewise is due to the rapid production of calcite at or near the site of injection. The problems with clogging and uneven calcite production are related to the difficulties associated with uniform transport of bacteria and attachment of bacteria to soil surfaces. Many factors affect the transport of bacteria through, and attachment to, soil grains including the properties of the cell surface, ionic strength of the carrier solution, flow rate, van der Waals forces, and pore space geometry within the soil matrix. Additionally, because the present method does not require the growth of one or more selected exogenous microorganisms that must be protected within a geomaterial, there is no need to fix microorganisms to the geomaterial prior to combining the necessary reagents for the method. Another advantage of the present method is that a large number of diverse urea-hydrolyzing microbial species are utilized in the present method, in contrast to the methods of the prior art in which a finite number of microbial species are utilized. Therefore, the present method obviates the need to manipulate the environment to favor one or more particular microbial species. Also, because the microbial population utilized in the current method is indigenous, the microorganisms used in this method are adapted to the local environment and are not at a competitive disadvantage in relation to microorganisms that are already in the geomaterial.

In addition to overcoming the disadvantages inherent to prior art methods, the current method provides a simpler and more robust method for forming a biocement. The method may be practiced in any geomaterial, does not require the culturing of microorganisms, and does not require steps such as fixing microorganisms in the geomaterial prior to practicing the method.

The source of nutrients that is utilized in the current method is any compound or combination of compounds that provides to microorganisms a source of energy and carbon, and preferably a source of trace minerals and vitamins. Examples of suitable nutrient sources include carbohydrates such as monosaccharides, disaccharides, oligosaccharides, and polysaccharides such as starch and cellulose; organic acids or their salts such as aliphatic, aromatic, and amino acids; casamino acids; hydrocarbons such as aliphatic and aromatic hydrocarbons; fatty acids or substituted acids such as keto-acids and hydroxy-acids; sugar alcohols such as glycerol and mannitol; multifunctional acids such as citrate; pyridines; purines; pyrimidines; biomass hydrolysate; molasses; yeast extract; corn steep liquor; peptones; tryptone; soytone; nutrient broth, and industrial waste stream products such as whey. A preferred nutrient source is molasses. Another preferred nutrient source is acetate, such as sodium acetate. In an especially preferred embodiment, molasses and acetate are utilized in combination as a nutrient source.

The source of calcium that is utilized in the current method is any source from which calcium ions may be obtained upon addition to the geomaterial or by action of microorganisms present in the geomaterial. Thus, the source of calcium may be any organic or inorganic calcium source of calcium ions, such as a calcium salt. A preferred calcium source is calcium chloride. Another preferred calcium source is calcium nitrate.

The urea may be provided in various forms. Preferably, the urea is provided as an aqueous solution in water.

Although the conversion of calcium carbonate as vaterite to calcite occurs in the presence of water, it is generally not necessary to add water to the geomaterial because even small amounts of water such as naturally found in geomaterials is sufficient. However, if desired, water may also be added. Such water may be added, for example, as a transporting medium used to deliver the reactants utilized in the current method.

The geomaterial utilized in the present method may be varied provided that it has a structure with interconnected pores or fractures and contains within it a population of microorganisms that are capable of hydrolyzing urea. For example, the geomaterial may be rock, typically sedimentary rock such as a terrigenous, chemical/biochemical or organic sedimentary rock. Examples of sedimentary rock that are suitable for the present method include conglomerate, breccia, sandstone, siltstone, shale, limestone, gypsum, dolostone, and lignite. As another example, either as an alternative to or in combination with rock, the geomaterial may be unconsolidated or partially consolidated porous medium such as soil (e.g. gravel, sand, silt, clay with or without organics such as peat) or sediments. The geomaterial of the present method may also be fractured igneous or metamorphic rock: Volcanic rock containing interconnected pores may also be utilized as the geomaterial of the present method.

It is not necessary to determine the identity of particular microorganisms that may be present in the geomaterial because geomaterials such as listed above contain a wide variety of suitable microorganisms. However, it may be helpful to describe particular microorganisms that may be present in a particular geomaterial. The microorganisms that are suitable for the method of the invention may constitutively express urease so that urease is expressed regardless of ammonia or nitrogen compound concentration. Such organisms include the following bacteria: *Sporosarcina pasteurii*, *Sporosarcina ureae*, and *Pseudomonas aeruginosa*. Other microorganisms that are suitable for the method of the invention include those in which urease is expressed only in the presence of urea. An example of a bacterium in which urease is expressed only in the presence of urea is *Proteus vulgaris*. Since there exist many bacteria that are able to hydrolyze urea in geomaterials that have never been isolated or characterized, the organisms listed here are meant to be examples. Many other known microbial genera and even previously unknown phylogenetic microbial groups present in geomaterials likely have the same capabilities for urea hydrolysis and are inherently included among the preferred indigenous microorganisms to be used in the present method.

Various tests exist that are suitable to determine if a geomaterial contains a microorganism that is capable of hydrolyzing urea. One such test is the Rapid Urease Test, also known as the CLO test (*Campylobacter*-like organism test), which is utilized in the medical field as a rapid test for diagnosis of *Helicobacter pylori*. The basis of the test is the ability of *H. pylori* to secrete the urease enzyme, which catalyzes the conversion of urea to ammonia and bicarbonate. The test is performed by placing a sample of a geomaterial into a medium containing urea and a pH sensitive indicator such as phenol red. If the sample contains urease, the urea in the medium will be converted to ammonia, which raises the pH of the medium and changes the color of the specimen from yellow (negative) to red (positive).

In accordance with the present method, the reactants may be added simultaneously or sequentially. In a preferred embodiment, the method utilizes an "enrichment phase" in which a geomaterial is enriched with an added source of nutrients which generally encourages the growth of microorganisms within the geomaterial. If desired, urea may be added during the enrichment phase to specifically encourage the growth of ureolytic microorganisms within the geomaterial. Optionally, a source of calcium ions may or may not be added during the enrichment phase. The concentration of the source of nutrients added to the geomaterial is that which is sufficient to encourage the growth of microorganisms within the geomaterial and will vary depending primarily on the particular source of nutrients that is added. It is conceived that if molasses is utilized as a source of nutrients, a preferred concentration of molasses is between about 0.005% to 0.05% by volume of the nutrient source. However, lower or higher concentrations of molasses may be added to a geomaterial so long as the concentration of molasses that is added is sufficient to encourage the growth of microorganisms with the geomaterial. Similarly, a preferred range of concentration of sodium acetate is 10mM to 150 mM. However, as with molasses, lower or higher concentrations of sodium acetate may be utilized.

As stated above, urea may be added together with the nutrients. If urea was added during the enrichment phase, then it may not be necessary to add additional urea during a subsequent treatment phase. Regardless of whether or not urea was included in the enrichment phase, it is preferred that urea is added in a "treatment phase" following the enrichment phase. In the treatment phase, the urea is added to the geomaterial preferably together with additional nutrients. The hydrolysis of urea to produce ammonia raises the pH and inhibits the growth of bacteria that do not thrive in the presence of elevated urea or ammonia concentrations or at elevated pH. The concentration of urea that is added to the geomaterial is that which is sufficient to produce sufficient carbonate to yield the desired degree of cementation of the geomaterial. A preferred range of urea concentration that is added to the geomaterial is between 250 mM to 2 mM. Concentrations of urea lower than 250 mM, for example as low as 50 mM or even lower, may be utilized. However, the desired rise in pH and production of carbonate ions will be slowed. Concentrations of urea higher than 2 mM may also be utilized, such as up to 2000 mM or higher. A preferred concentration of urea is between 250 to 333 mM.

As part of the treatment phase, a source of calcium ions is added, either together with or following the urea, which reacts with the carbonate ions produced as a result of hydrolysis of urea to form calcium carbonate. The concentration of calcium ions added may be varied, with lower concentrations resulting in a slower process of cementation and higher concentrations resulting in a faster process of cementation. Generally, a source of calcium ions is added to provide a concentration of calcium ions of at least about 10 mM. The concentration of calcium ions is preferably no higher than that of urea, but may be higher if desired. For example, the concentration of calcium ions added to the geomaterial may be up to 2000 mM or higher. A preferred concentration of calcium ions is about 250 mM. Preferably, additional iterations of the treatment phase may be performed by adding to the geomaterial one or more of urea, nutrients, and calcium ions, which further select for ureolytic bacteria that can survive at high pH.

It is preferred, although not essential, that two or more, preferably at least five, and more preferably, at least ten iterations of the treatment phase by adding one or more of urea, a nutrient source, and a calcium ion are performed. It is most preferred that at least two of these reactants and preferably all three of these reactants are added at each iteration. It has been found that pH rises more rapidly with successive iterations, which is conceived to be due to the microbial population in a geomaterial becoming more and more exclusively composed of microorganisms that are ureolytic and that can survive at elevated pH. Further, with additional iterations, the quality of cementation of the geomaterial is enhanced as more and more calcite is produced.

Although the preferred embodiment of the present method is described which includes sequential enrichment and treatment phases, it is not necessary for the present method that the enrichment and treatment to be in separate phases. If desired, a source of nutrients, urea, and a source of calcium may be added to a geomaterial in order to encourage the growth of ureolytic microorganisms, to permit the ureolytic microorganisms to hydrolyze urea and produce carbonate ions, and to permit the carbonate ions to combine with calcium ions to form calcium carbonate. It is preferred, although not essential, that two or more, preferably at least five, and more preferably, at least ten iterations of the addition of one or more of urea, a nutrient source, and a calcium ion are performed. It is most preferred that at least two of these reactants and preferably all three of these reactants are added at each iteration.

The reactants may be added to the geomaterial in any manner by which the reactants are made available to microorganisms within the geomaterial. For example the reactants may be added under pressure, such as by flushing or injecting, such as in an aqueous solution, into or onto the geomaterial or by spraying, dripping, or trickling the reactants onto or into the geomaterial.

The invention is further illustrated in the following non-limiting examples. All concentrations mentioned below are % w/w unless otherwise indicated.

EXAMPLE 1

CaCO$_3$ Precipitation From Soil Samples

Soil samples were collected at depths of 30 cm, 60 cm, 90 cm, and 150 cm from the shore of the Snake River, about 5 miles south of the Lower Granite Dam in Washington State using a stainless steel augur. Collected samples were placed directly into sterile 30 ml Becton Dickenson syringes which were sealed at the bottom to prevent leakage but remained exposed to air at the top. The samples were placed on ice for transport to the Environmental Biotechnology Institute at the University of Idaho in Moscow, Idaho. All samples were collected from beneath the water table and initial pH and temperature measurements were taken using an Acorn® pH 6 series meter (Oakton Instruments, Vernon Hills, Ill). Samples were stored at 4° C. prior to treatment and were treated within 14 hours of collection. Water was collected from the Snake River from an area adjacent to where the soil samples were collected and was stored on ice for transit and at 4° C. between uses.

Soil samples were treated with an enrichment medium of an aqueous solution containing a carbon nutrient source of a combination of 1.0% molasses (Grandma's Molasses, unsulfured, Motts USA, Rye Brook, N.Y.) and 170 mM sodium acetate (CH$_3$COONa.3H$_2$O) (Research Organics, Inc., Cleveland, Ohio) and also containing 250 mM urea (Thermo Fisher Scientific, Waltham, Mass.) 250 mM CaCl$_2$.2H$_2$O (reagent grade, EMD Chemicals Inc., Gibbstown, N.J), 12.2 mM NH$_4$Cl (Thermo Fisher Scientific), and 0.1 g Bacto yeast extract (Becton Dickenson, Franklin Lakes, N.J) per liter of distilled water at pH 7.0 for 7 days followed by three treatments spaced 72 hours apart with a biomineralization medium containing 50 mM sodium acetate, 50 mM CaCl$_2$, 333 mM urea, 12.2 mM NH$_4$Cl, and 0.1 g yeast extract per liter of distilled water at pH 7.0.

Negative controls were maintained in parallel. Control samples were treated with sterile phosphate buffered saline containing, per liter of distilled water, 8 g NaCl, 0.2 g KCl, 1.44 g Na$_2$HPO, at pH 7.4.

The percentage of CaCO$_3$ was then determined as follows. Control syringes containing untreated samples from soil collected at each depth and the treated syringes following treatment were flushed with approximately five pore volumes of 50 mM NaCl to remove organics and poorly bound CaCO$_3$. About 5 mm of soil from the top of each column was removed and discarded to remove carbonates that may have precipitated and accumulated on the soil surface. The soil samples were then dried in an oven for 24 hours at 121° C., weighed, and washed with approximately five pore volumes of 1 M HCl to dissolve the calcium carbonate, then rinsed with nanopure water and again dried for 24 hours. The soil samples were weighed again and the difference in weight was attributed to the weight of calcium carbonate in the treated sample.

The average concentration of CaCO$_3$ in the treated samples was 2.8% w/w.

EXAMPLE 2

CaCO$_3$ Precipitation From Soil Samples Using a Lower Concentration of Added Nutrients The study of Example 1 was repeated except that the soil samples were treated with a carbon nutrient source of a combination of 0.1% molasses and 50 mM sodium acetate. The average concentration of CaCO$_3$ in the treated samples was 2.2% w/w.

EXAMPLE 3

CaCO$_3$ Precipitation From Soil Samples Using a Single Source of Carbon

The study of Example 1 was repeated except that the soil samples were treated with a carbon nutrient source of 150mM sodium acetate and lacking molasses. The average concentration of CaCO$_3$ in the treated samples was 1.8% w/w.

EXAMPLE 4

CaCO$_3$ Precipitation From Soil Samples Using a Single Source of Carbon

The study of Example 1 was repeated except that the soil samples were treated with a carbon nutrient source of 0.5% molasses and lacking sodium acetate. The average concentration of CaCO$_3$ in the treated samples was 0.92% w/w. The studies of Examples 1 to 4 show that, although a particular nutrient source or combination of nutrient sources may be utilized to optimize the present method, the method may be successfully performed using any source of nutrients that can be utilized by microorganisms in a geomaterial.

EXAMPLE 5

CaCO$_3$ Precipitation From Soil Samples Using Different Concentrations of Calcium Ions The study of Example 1 was repeated using soil samples that were collected from beneath the water table at depths of 46 cm, 90 cm, and 150 cm from the shore of the Snake River. Approximately 1.05 pore volumes of an enrichment medium containing a combination of either 50 mM or 250 mM CaCl$_2$, 0.5% molasses, 170 mM sodium acetate, 333 mM urea, 12.2 mM NH$_4$Cl, and 0.1 g Bacto yeast extract per liter of distilled water at pH 7.0 was added to each column for 72 hours. This was followed by seven treatments spaced 1 to 3 days apart with approximately 1.05 pore volumes of a biomineralization medium containing either 50 mM or 250 mM CaCl$_2$, 170 mM sodium acetate, 333 mM urea, 12.5 mM NH$_4$Cl, and 0.1 g yeast extract per liter of distilled water at pH 7.0.

Negative controls were maintained in parallel. Control columns were treated with 1.05 pore volumes of the enrichment medium containing either 50 or 250 mM CaCl$_2$ but lacking urea. Additional negative controls were treated with approximately 1.05 pore volumes of water collected from the Snake River, which was treated in the same manner as the other samples.

The percentage of CaCO$_3$ in each sample was then determined as in Example 1. Results are shown below in Table 1.

TABLE 1

| Effect of Calcium Concentration on % Calcite | |
|---|---|
| Sample | % Calcium Carbonate (calcite) |
| 46 cm depth, low Ca concentration | 2.124 |
| 46 cm depth, high Ca concentration | 3.478 |
| 90 cm depth, low Ca concentration | 2.412 |
| 90 cm depth, high Ca concentration | 3.640 |
| 150 cm depth, low Ca concentration | 3.876 |
| 150 cm depth, high Ca concentration | 4.520 |

As shown in Table 1, higher calcium concentrations utilized in the media yielded higher calcite production in soil samples treated according to the present method. No calcite or other forms of calcium carbonate were detected in control soil samples treated in the same manner as the samples treated in accordance with the present method except for the omission of urea. No calcite of other forms of calcium carbonate was detected in water collected from the Snake River. Calcium carbonate was detected only in columns containing soil in which the indigenous microorganisms were treated with medium that contained urea and calcium chloride, thus ruling out the possibility that calcite was either already present in the soil prior to treatment or was precipitated by some process other than by microbial hydrolysis of urea.

Various modifications of the above described invention will be evident to those skilled in the art. It is intended that such modifications are included within the scope of the following claims.

The invention claimed is:

1. A method for increasing the concentration of calcium carbonate in a geomaterial comprising specifically encouraging the growth of indigenous alkalinity-tolerant and ureolytic microorganisms within the geomaterial, which promoting comprises adding a source of nutrients and urea to a geomaterial that contains indigenous microorganisms that are capable of hydrolyzing urea to ammonia, and adding a source of calcium ions to the geomaterial thereby promoting the production of calcium carbonate within the geomaterial by the ureolytic microorganisms.

2. The method of claim 1 wherein the addition of the source of nutrients is performed prior to the addition of urea and the source of calcium ions.

3. The method of claim 1 wherein the addition of the source of nutrients is performed substantially simultaneously with the addition of urea.

4. The method of claim 3 wherein the addition of the source of calcium ions is performed substantially simultaneously with the addition of the nutrients and the urea.

5. The method of claim 1 wherein the calcium carbonate that is produced by the microorganisms is calcite.

6. The method of claim 1 wherein one or more of the nutrient sources, the urea, and the source of calcium are added a multiplicity of times to the geomaterial.

7. The method of claim 1 wherein the geomaterial is selected from the group consisting of soil and rock.

8. The method of claim 1 wherein no exogenous microorganisms are added to the geomaterial.

9. A method for increasing the concentration of calcium carbonate in a geomaterial comprising enriching the geomaterial with a source of nutrients to encourage the growth of microorganisms already contained within the geomaterial, adding urea to the geomaterial, and adding a source of calcium ions to the geomaterial, thereby promoting the production of calcium carbonate within the geomaterial.

10. The method of claim 9 which consists essentially of enriching the geomaterial with a source of nutrients to encourage the growth of microorganisms already within the geomaterial, adding urea to the geomaterial, and adding a source of calcium ions to the geomaterial, thereby promoting the production of calcium carbonate within the geomaterial.

11. The method of claim 1 which consists essentially of the promoting the growth of indigenous alkalinity-tolerant and ureolytic microorganisms within the geomaterial and the adding of a source of calcium ions to the geomaterial.

* * * * *